United States Patent [19]

Haddad et al.

[11] 3,948,732

[45] Apr. 6, 1976

[54] CELL CULTURE ASSEMBLY

[75] Inventors: Ihsan A. Haddad, Bedford; Alvin R. Arsenault, Burlington, both of Mass.

[73] Assignee: Instrumentation Laboratory, Inc., Lexington, Mass.

[22] Filed: Aug. 22, 1974

[21] Appl. No.: 499,515

Related U.S. Application Data

[63] Continuation of Ser. No. 365,535, May 31, 1973, Pat. No. 3,887,436.

[52] U.S. Cl. ............... 195/127; 195/142; 195/109; 195/118; 195/1.8
[51] Int. Cl.² .......................................... C12B 1/00
[58] Field of Search ........... 195/127, 139, 142, 109; 23/258.5

[56] References Cited
UNITED STATES PATENTS

| 3,738,813 | 6/1973 | Esmond | 23/258.5 |
| 3,757,955 | 9/1973 | Leonard | 23/258.5 |
| 3,853,712 | 12/1974 | House et al. | 195/127 |

OTHER PUBLICATIONS

Nosé, Manual on artificial organs, Vol. II The Oxygenator. Pub. by The C. V. Mosby Co. pp. 127-162 (1973).

Primary Examiner—Alvin E. Tanenholtz

[57] ABSTRACT

A replaceable, sterilizable, cell growth assembly comprising a chamber structure of gas permeable, liquid impermeable material having an inner surface to which cells are attachable. The chamber is of tubing configuration and is disposed in a plurality of layers in stacked relation. Spacer structure between the layers of tubing define a plurality of flow passages between the layers and enable a gaseous environment to bathe the majority of the external surface area of the tubing layers. The chamber also includes an inlet conduit for introducing culture media for flow through the plural layers of the chamber structure and an outlet conduit for receiving culture media from the chamber structure, and coupling structure for detachably connecting the inlet conduit to a source of culture media and the outlet conduit to an appropriate culture media receptacle.

9 Claims, 4 Drawing Figures

CELL CULTURE ASSEMBLY

This application is a continuation in part of our copending patent application Ser. No. 365,535, filed May 31, 1973 now U.S. Pat. No. 3,887,436, entitled "Fluid Handling".

SUMMARY OF INVENTION

This invention relates to the growth of living cells, and more particularly to systems for such cell culture and chambers for use in such systems.

The culture of cells in monolayer films is well known and has permitted very rapid development of virological techniques and the manufacture of antiviral vaccines from viruses produced in vitro under reproducible and readily controllable conditions.

Numerous cell propagation arrangements have been proposed in which conditions are established which approach a cell environment in the intact animal. Such cell propagation arrangements include the use of stationery "Roux" flasks, and "roller" bottles, the tissue culture chambers typically being of glass or plastics materials. Another example of a proposed system is described in the article "Cell Propagation of Films of Polymeric Fluorocarbon as a Means to Regulate Pericellular pH and $PO_2$ in Cultured Monolayers", Munder et al. FEBS Letters, Volume 15, No. 3, June 1971, page 191. A particular need exists for improved large scale cell culture systems.

An object of this invention is to provide a novel and improved cell culture system.

Another object of this invention is to provide an improved tissue culture or cell growth chamber for use in large scale culturing of cells or similar materials, for example cells of animal origin.

In accordance with a feature of the invention there is provided a replaceable, sterilizable, cell growth assembly comprising a chamber structure of gas permeable, liquid impermeable material having an inner surface to which cells are attachable. The chamber is of tubing configuration and is disposed in a plurality of layers in stacked relation. Spacer structure between the layers of tubing define a plurality of flow passages between the layers and enable a gaseous environment to bathe the majority of the external surface area of the tubing layers. The chamber also includes an inlet conduit for introducing culture media for flow through the plural layers of the chamber structure and an outlet conduit for receiving culture media from the chamber structure, and coupling structure for detachably connecting the inlet conduit to a source of culture media and the outlet conduit to an appropriate culture media receptacle.

In a particular embodiment, the sample chamber is an elongated tubular member disposed in spiral configuration and both the inlet and outlet conduits are of flexible resilient tubing, the ends of which provide the detachable coupling structure. The chaamber is made of a sheet of fluorinated ethylene-propylene copolymer, one surface of which has been chemically etched although other suitable gas permeable liquid impermeable materials may be used. The spacer structure may take a variety of forms, for example, a sheet member to which are secured on each side a multiplicity of uniformly spaced protrusions, an embossed sheet, or a sheet of "expanded metal" configuration. In a particular embodiment the spacer structure includes a convoluted strip member that is disposed between adjacent turns or layers of the spiral configuration chamber, providing positive support of those layers, maintaining them spaced from one another and defining a multiplicity of transverse flow passages extending along its length. The convolutions or other support portions of the spacer structure provide small and closely spaced support areas so that the chamber wall does not sag into contact with the spacer structure at points between the support portions and the majority of the external chamber surface area is spaced from the spacer structure, providing multiple gas flow paths across the external surfaces of each layer. Supplemental spacer portions are preferably provided along each edge of each interposed spacer sheet to maintain the stacked sheets of the spacer structure spaced from one another to provide the requisite gas flow paths. Thus nutrient media may be flowed through the chamber from the inlet conduit to the outlet conduit to bathe cells attached to the inner surfaces of the multilayer chamber and gases in the area surrounding the chamber diffuse through the chamber walls into the chamber.

This invention provides a replaceable culture chamber which provides particular convenience for use in arrangements adapted for large scale and efficient cell culture.

In accordance with another feature of the invention there is provided a cell culture system comprising a housing, a cell culture substrate in the housing, the cell culture substrate being of gas permeable, liquid impermeable material and having a first surface to which cells are attachable and an opposite surface exposed to the gaseous environment in the housing. A nutrient media circulation path includes supply and return conduits connected to the cell culture substrate, means for circulating nutrient media along the circulation path and across the surface of the cell culture substraate to which cells are attachable, a redox sensor for monitoring the reduction-oxidation potential of nutrient media in the circulation path, and a control responsive to the redox sensor for controlling the gaseous environment in the housing and specifically controlling the introduction of oxygen to the housing for flow across the opposite surface of the cell culture substrate to provide a controlled atmosphere conducive to cell growth on the substrate.

Other objects, features and advantages of the invention will be seen as the following description of a particular embodiment progresses, in conjunction with the drawings, in which.

DESCRIPTION OF PARTICULAR EMBODIMENT

Figure 1:
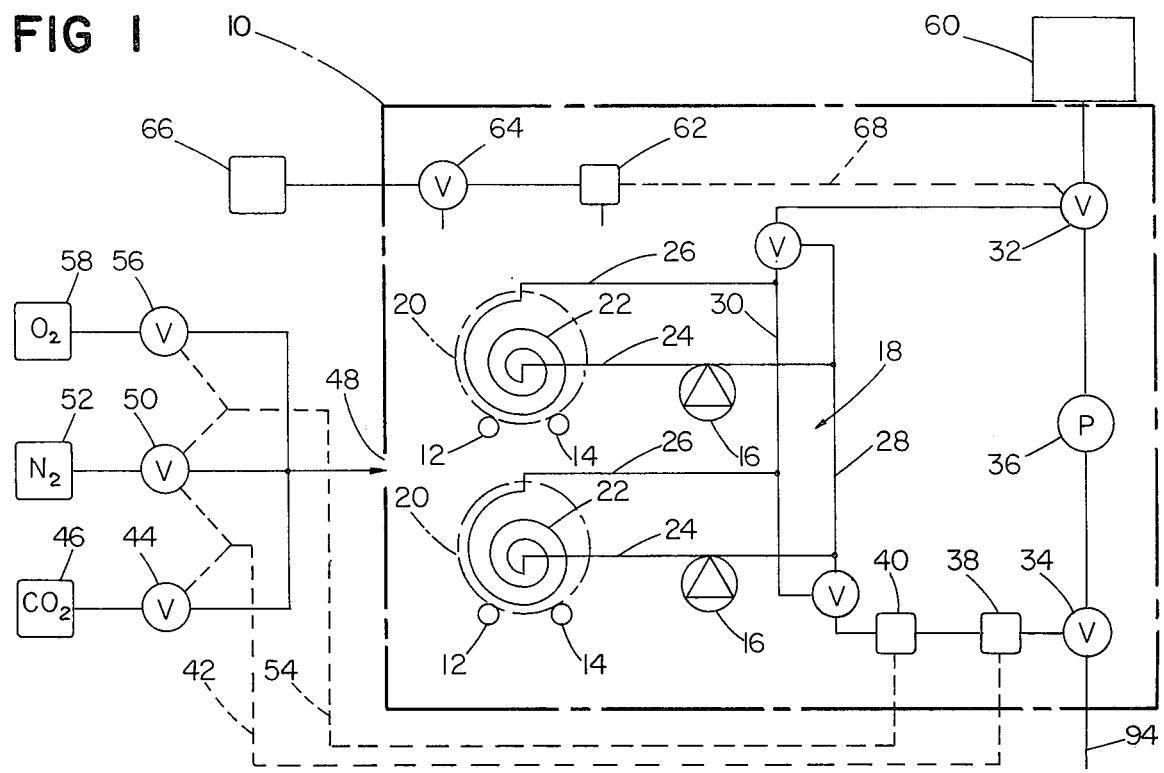
FIG. 1 is a diagram indicating aspects of a cell culture system in accordance with the invention.

With reference to FIG. 1, there is diagrammatically shown a housing in the form of incubator 10, the interior of which is held at a precisely controlled, uniform temperature by suitable heating sources and controls in conventional manner. Disposed in incubator 10 are cell culture chamber support structure in the form of roller elements 12, 14; a series of peristaltic pump cages 16; and a manifold structure 18. Mounted on roller elements 12, 14 are a series of detachable cell culture chamber units 20, each chamber unit including an elongated tubular chamber 22, an inlet conduit 24 and an outlet conduit 26. Each conduit 24, 26 is of stretchable tubing and its end may be resiliently forced over a cooperating fitting in a detachable coupling arrangement. Inlet conduit 24 is trained over the cage of the corresponding peristaltic pump cage 16 and connected to one leg 28 of manifold 18 while the outlet or discharge conduit 26 is connected to the other leg 30 of manifold 18. Connected between manifold legs 28, 30 is a circulation loop that includes valves 32, 34, pump 36, pH sensor unit diagrammatically indicated at 38 and redox sensor unit diagrammatically indicated at 40.

The pH sensor unit 38 monitors the hydrogen ion activity of the nutrient material circulating in the system and includes a pH sensitive electrode, e.g. a glass electrode, and a reference electrode, e.g. a calomel electrode, and meter apparatus for measuring the potential difference between the two electrodes. The redox sensor unit 40 includes a sensor electrode, e.g. a platinum electrode, and a reference electrode, e.g. a calomel electrode, and meter apparatus for measuring the potential difference between the two electrodes. The output of the pH sensor unit is applied over line 42 to control valve 44 which controls the flow of carbon dioxide from source 46 into the incubator housing through port 48. Sensor unit 38 also has a connection to control valve 50 which controls the flow of nitrogen from source 52 into housing 10 for moderating purposes. Similarly redox sensor unit has an output over line 54 which is applied to valve 56 for control flow of oxygen from source 58 into housing 10 and also a connection to valve 50 which enables moderating introduction of nitrogen from source 52.

Nutrient media is supplied to the system from source 60 through valve 32 which, during system operation, is under control of carbon dioxide sensor 62 which is arranged normally to monitor the carbon dioxide in housing 10. A source of calibrated carbon dioxide 66 may be connected to sensor 62 via valve 64 as periodic calibration of sensing unit 62 is desirable. Accordingly, valve 64 is periodically operated, for example 1 minute for each hour of system operation, and the flow of calibrated carbon dioxide from source 66 past sensor 62 provides a calibration or reference signal. This calibration signal is stored and through the remainder of the operating cycle, valve 64 is positioned so that sensor 62 monitors the carbon dioxide content in the incubator, the output of sensor unit 62 over line 68 controlling valve 32. Additional details concerning aspects of the culture nutrient media flow path and the manifold structure 18 in a particular embodiment may be had with reference to our copending parent application Ser. No. 365,535, filed May 31, 1973, entitled "Fluid Handling".

Figure 2:
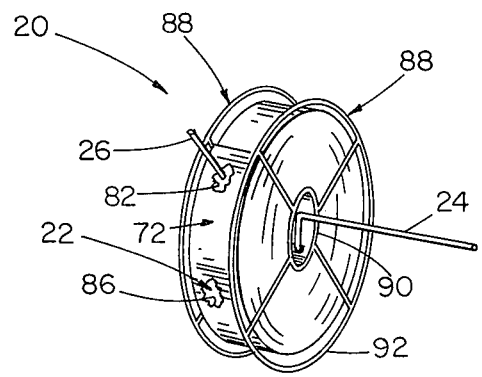
FIG. 2 is a perspective view of a cell culture unit in accordance with the invention.
Figure 3:
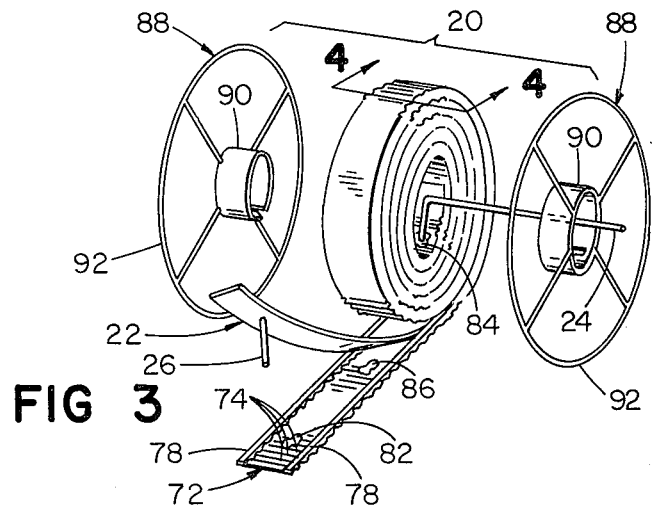
FIG. 3 is an exploded perspective view of components of aa cell culture chamber unit of FIG. 2.
Figure 4:
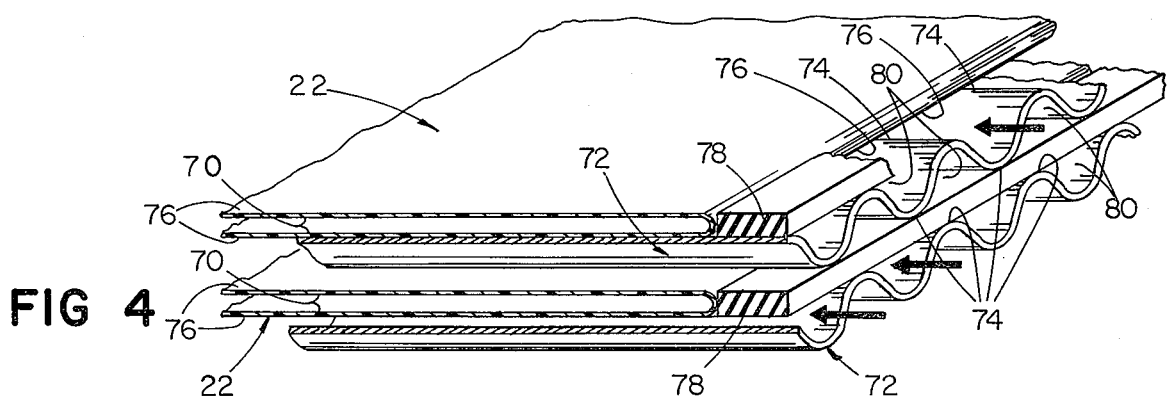
FIG. 4 is a perspective view on an enlarged scale taken along the line 4—4 of FIG. 3.

Further details of the detachable cell culture unit 20 may be seen with reference to FIGS. 2–4. Each cell culture unit includes an elongated tubular chamber 22 which, in a particular embodiment, has a length of 24 feet and a width of 2 inches. The chamber in that embodiment is made of a sheet (1 mil thick) of fluoroethylene-propylene copolymer (Teflon FEP), one surface 70 of which has been chemically etched. This sheet is folded in half and the two longitudinal edges heat sealed together. The heat sealed edge is then folded over and that edge portion is secured in place along the length of the chamber by adhesive tape. A similar seal is made at each end. The composite seals provide a chamber that is steam sterilizable and withstands fluid pressure of flowing nutrient media. Connected to one end of tube 22 is inlet conduit 24 and connected to the other end of tube 22 is outlet conduit 26. Each conduit 24, 26 is stretchable tubing so that its end may be resiliently forced over a cooperating fitting for connection to manifold 18 in a detachable coupling arrangement. This chamber is impermeable to liquids by permeable to gases and its chemically etched inner surface 70 provides a substrate surface to which the cells to be cultured adhere.

Chamber tube 22, as indicated in FIG. 3, is spirally wound with an interleaved, elongated spacer member 72 that has a multiplicity of spaced projecting support portions 74. In particular embodiments, the spacer member 72 is 0.003 inch gauge steel or 0.005 inch gauge aluminum that is a 2¾ inch in width and the spaced support portions 74 are formed by convolutions or corrugations that are spaced about 0.1 inch apart and have a height of about 0.04 inch, the corrugated support portions 74 extending the full transverse width of the chamber 22 and providing spaced support portions 74 on opposite sides of the spacer member 72 of relatively small area with larger area between adjacent support portions 74 so that the external surface 76 of the chamber on either side of each support portion 74 is exposed, as indicated in FIG. 4. The spacer portions 74 may be continuous across the width of the spacer member 72 or interrupted and may be spaced in various manners, for example uniformly or randomly provided that sufficient exposed substrate area is provided to supply the requisite gaseous support for cell growth over the entire substrate surface 70. In this embodiment, supplemental spacer strips 78 of silicone rubber are disposed along each side of the spacer member 72 along its length, each supplemental spacer strip 78 being about one eighth inch in width and one thirty-second inch in height and suitable bonded to the spacer member 72. The supplemental spacer strips 76 maintain the adjacent layers of the spacer member 72 spaced from one another and maintain channels 80 of large area through which gas may flow across the external surfaces 76 of the chamber layers 22 between the layers of spacer member 72. Provided in spacer member 72 are port 82 through which inlet conduit 24 passes, port 84 through which outlet conduit 26 passes, and a viewing port 86 through which cell growth may be observed. Flange members 88 (FIGS. 2 and 3) have hub portions 90 which provides support for the multilayer cell culture chamber 22, protective side portions, and circular rim portions 92 which rest on roller support members 12, 14 (FIG. 1).

On loading a chamber unit 20 into the incubator housing 10, the chamber reel flange peripheries 92 are positioned on roller supports 12, 14, each corresponding inlet line 24 is trained about its respective peristaltic pump cage 16, and the conduit ends are detachably connected to manifold 18. The manifold passages 28, 30 are filled with liquid nutrient from supply 60 (either prior or subsequent to connecting the culture chambers 20) via valve 32.

The cells or tissue may be introduced into chambers 20 through one of the terminal openings together with an amount of nutrient material, or a cell suspension may be injected through the wall of the chambeer into the nutrient material by means of a syringe. The puncture is sealed spontaneously by the resilient sheet chamber material upon withdrawal of the needle. During filling of the spiral chambers 20 with nutrient material, the reels are preferably driven in rotation at a low rate of speed (first about 360° in one direction and then 360° in the opposite direction) to assist in displacing gases from the chamber and to improve contact of the nutrient material with the cells. After the cells are introduced and distributed through the spiral chamber, the system is maintained in static condition for interval of time to facilitate attachment of the cells to the roughened interior walls 70 of the chambers 22.

While cells are being grown in chambers 22, the incubator 10 is held at the desired condition of humidity and temperature, typically 37° C. Nutrient material is circulated between the manifold 18 and the chambers 22. pH sensor 38 monitors the hydrogen ion concentration in the circulating nutrient material and its output signal is applied to control the introduction of carbon dioxide and moderating nitrogen into the incubator chamber 10 to maintain the pH of the liquid nutrient material at a selected value, typically about 7. Redox sensor 49 similarly monitors the redox potential of the nutrient material and its output signal is applied to control the introduction of oxygen and moderating nitrogen in the incubator chamber 10 to control the redox potential of the liquid nutrient material. (In another embodiment the oxygen content in housing 10 is monitored by an oxygen sensor located in the housing and a proportional control valve (e.g. valves 50 and 56) are controlled by that sensor to maintain the gas phase $pO_2$ at 126–135 mmHg). The carbon dioxide content of the incubator chamber is monitored by carbon dioxide sensor 62 as indicated above, and when the accumulation of components, such as lactic acid which is produced by many growing cells, in the circulating nutrient material makes it impossible to maintain the desired pH by reducing the amount of carbon dioxide in the chamber, the output of sensor 62 shifts valves 32 and 34 so that at least a portion of the circulating nutrient material is transferred through discharge line 94 and replaced by fresh media uncontaminated by products of cell metabolism from supply 60. The inner substrate surfaces 79 and the layers of the tubular chamber 22 are maintained in spaced relation so that the nutrient media can flow through the chamber 22 with the gas phase in incubator 10 being maintained in gas equilibrium with the nutrient media through the permeable walls of the chamber 22. Adequate interchange of the gas phase across the outer surfaces 76 of the chamber 22 is assured by the large exposed area of those surfaces and the flow passages 80 provided by the spacer member 72. The apparatus provides an advantageous controlled atmosphere cell culture chamber arrangement which is particularly useful with gas permeable chambers of etched FEP Teflon to produce multilayer cell cultures as described in Jensen et al., "Comparative Growth Characteristics of VERO cells on Gas-Permeable and Conventional Supports", 84 Experimental Cell Research 271–281 (1974).

While a particular embodiment of the invention has been shown and described, various modifications thereof will be apparent to those skilled in the art and therefore it is not intended that the invention be limited to the disclosed embodiment or to details thereof, and departures may be made therefrom within the spirit and scope of the invention.

What is claimed is:

1. A replaceable, sterilizable cell growth assembly comprising a tubular chamber of gas permeable liquid impermeable material having an inner surface to which cells adhere, said chamber being disposed in a plurality of layers in stacked relation, spacer structure between adjacent layers of said chamber maintaining said adjacent layers spaced from one another to permit gas to contact external surfaces of said layers over substantially their entire lengths, supply conduit structure connected to said plural layer chamber for introducing culture media for flow through each plural layer chamber, and return conduit structure connected to said plural layer chamber for receiving culture nutrient media from said plural layer chamber structure, said supply and return conduits each being adapted to be detachably connected to cooperating structure.

2. The assembly as claimed in claim 1 wherein said chamber is of spiral configuration and defines an elongated nutrient media flow path between said supply and return conduits.

3. The assembly as claimed in claim 1 wherein said spacer structure is sheet member structure that has a plurality of spaced projections on either side, said projections supporting said chamber and providing plural flow passages over the outer surface of said chamber, the area of the outer surface of said chamber exposed to said flow passages being greater than the area of the outer surface of said chamber in supported engagement with said projections so that adequate gaseous growth support is supplied to cells attached to the inner surface of said chamber.

4. The assembly as claimed in claim 3 wherein said spacer structure further includes supplementary spacer members disposed between adjacent layers of said sheet member to maintain surfaces of said sheet member spaced from one another and a flow path for nutrient media through said chamber.

5. A replaceable, sterilizable cell growth assembly comprising a tube of gas permeable, liquid impermeable organic plastic that has a roughed inner surface to which cells adhere, said tube being disposed in a plurality of layers in stacked relation, portions of said inner surface in each layer being disposed in opposed spaced relation and defining a passage for flow of culture media through said passage, spacer structure between adjacent layers of said tube maintaining the spacing of said opposed inner surface portions from one another to provide said culture media flow passage and the spacing of said adjacent layers from one another to permit gas to contact external surfaces of said tube over substantially the entire length of said tube, supply conduit structure connected to one end of said tube for introducing culture media for flow through said tube, and return conduit structure connected to the other end of said tube for receiving culture media from said tube, said supply and return conduits each being adapted to be detachably connected to cooperating structure for flowing culture media under pressure through said tube to nourish cells attached to said inner surface portions.

6. The assembly as claimed in claim 5 wherein said spacer structure is an embossed elongated transversely corrugated strip providing structure disposed between adjacent layers of said tube and passages for flow of gas transversely of said tube along the length thereof, said strip structure having a multiplicity of spaced transversely extending projection portions supporting said tube in spaced relation from other portions of said spacer structure to provide plural transversely extending channels, permitting flow of gas over external surfaces of said tube and a flow path for nutrient media through said tube.

7. The assembly as claimed in claim 6 wherein said tube is of spiral configuration and defines an elongated nutrient media flow path between said supply and return conduits.

8. The asembly as claimed in claim 7 wherein said spacer structure further includes supplementary spacer members disposed between adjacent layers of said corrugated strip to maintain surfaces of said corrugated strip spaced from one another and a flow path for nutrient media through said tube.

9. The assembly as claimed in claim 1 wherein said chamber is a tube of organic plastic that has a roughed inner surface that enhances the facility of attachment by cells to that surface.

* * * * *